United States Patent
Ji

(10) Patent No.: US 10,139,165 B2
(45) Date of Patent: Nov. 27, 2018

(54) APPARATUS FOR PRODUCING NANOPARTICLES

(71) Applicant: ECOPICTURES CO., LTD, Seoul (KR)

(72) Inventor: Jun-Ho Ji, Namyangju-si (KR)

(73) Assignee: ECOPICTURES CO., LTD, Seoul (KR)

( * ) Notice: Subject to any disclaimer, the term of this patent is extended or adjusted under 35 U.S.C. 154(b) by 154 days.

(21) Appl. No.: 15/123,219

(22) PCT Filed: Mar. 25, 2015

(86) PCT No.: PCT/KR2015/002912
§ 371 (c)(1),
(2) Date: Sep. 1, 2016

(87) PCT Pub. No.: WO2015/152563
PCT Pub. Date: Oct. 8, 2015

(65) Prior Publication Data
US 2017/0074587 A1   Mar. 16, 2017

(30) Foreign Application Priority Data
Apr. 1, 2014   (KR) ........................ 10-2014-0038761

(51) Int. Cl.
*F27B 17/00* (2006.01)
*G01N 15/02* (2006.01)
(Continued)

(52) U.S. Cl.
CPC ............ *F27B 17/0083* (2013.01); *B22F 9/04* (2013.01); *F27D 7/02* (2013.01); *F27D 21/00* (2013.01);
(Continued)

(58) Field of Classification Search
CPC ......................................................... B01J 6/00
See application file for complete search history.

(56) References Cited

U.S. PATENT DOCUMENTS

| | | | |
|---|---|---|---|
| 7,750,270 B2 * | 7/2010 | Ji ............................... | B01J 6/00 |
| | | | 219/201 |
| 7,846,414 B2 * | 12/2010 | Harbec .................. | B82Y 30/00 |
| | | | 204/173 |
| 7,863,545 B2 * | 1/2011 | Ji ............................... | B01J 6/00 |
| | | | 219/219 |

FOREIGN PATENT DOCUMENTS

| | | |
|---|---|---|
| KR | 10-2006-0075893 A | 6/2006 |
| KR | 10-2007-0014708 A | 2/2007 |

(Continued)

*Primary Examiner* — Scott R Kastler
(74) *Attorney, Agent, or Firm* — John P. White; Cooper & Dunham LLP

(57) ABSTRACT

Disclosed herein is a nanoparticle generator, comprising a body defining an internal space, with an electric insulator inserted into the internal space from a side of the body; a heat-insulating tube, internally inserted into the body, wherein the electric insulator and a local heating unit which is mounted on the electric insulator are internally inserted into the heat-insulating tube along a central axis thereof; a first inlet, provided at a side of the body, for introducing external air into the heat-insulating tube; a second inlet, provided at a side of the body, for introducing external air between the heat-insulating tube and the body; and an outlet, provided at a side of the body, for evacuating the air introduced through the heat-insulating tube into the body.

18 Claims, 4 Drawing Sheets

(51) Int. Cl.
*B22F 9/04* (2006.01)
*F27D 7/02* (2006.01)
*F27D 21/00* (2006.01)
*G01N 15/00* (2006.01)

(52) U.S. Cl.
CPC .... *G01N 15/0266* (2013.01); *B22F 2009/045* (2013.01); *G01N 2015/0038* (2013.01)

(56) References Cited

FOREIGN PATENT DOCUMENTS

| KR | 10-2007-0023137 A | 2/2007 |
| KR | 10-2007-0023138 A | 2/2007 |
| KR | 10-2008-0102268 A | 11/2008 |

* cited by examiner

APPARATUS FOR PRODUCING NANOPARTICLES

CROSS-REFERENCE TO RELATED APPLICATIONS

This application is a § 371 national stage of PCT International Application No. PCT/KR2015/002912, filed Mar. 25, 2015, claiming priority of Korean Patent Application No. KR 10-2014-0038761, filed Apr. 1, 2014, the content of each of which is hereby incorporated by reference into the application.

FIELD OF THE INVENTION

The present disclosure relates to a nanoparticle generator. More particularly, the present disclosure relates to a nanoparticle generator that can, generate a high concentration of non-aggregated nanoparticles at a low energy.

DESCRIPTION OF RELATED ART

Nanoparticles are solid or liquid phase particles between 1 nm and 100 nm in size. Characteristic physical and chemical properties that are not observed in bulk materials appear as their sizes approach the nano scale.

Recently, nanoparticles have been deeply involved in modern science. For example, nano-silver or nano-copper particles are used to eliminate bacteria. Studies have discovered that nano titanium dioxide and zinc oxide exhibit improved photocatalytic efficiency compared to their bulk materials. In addition, attempts have been made to construct nanoparticles of carbonic materials, such as carbon nanotubes, graphenes, etc., in order to obtain better properties than those of their bulk materials. Further, gold nanoparticles find applications in various fields including biological research, cancer diagnosis, sensor devices, etc. Some nanoscale materials have approached the stage of industrial usefulness.

The synthesis of nanoparticles frequently resorts to a vaporization-condensation method in which materials are vaporized with heat, after which the vapor is allowed to condense into nanometer-size particles. The conventional practice is illustrated as follows.

A conventional nanoparticle generator comprises an electric furnace in which a high temperature is established, and a tube passing through the electric furnace. The sample to be converted into nanoparticles by vaporization-condensation is placed in a high-temperature zone within the tube.

Under the condition that fluid such as air is allowed to travel through the tube, the electric furnace is operated to elevate the temperature in the high-temperature zone to vaporize the sample. Thus, the vapor flows together with the fluid.

When the vaporized sample is in contact with the air flowing through the tube, some of the vapor is chilled and condenses into nano- or sub-nano scale size particles which then grow into nanoparticles having a wide size distribution through aggregation therebetween.

The conventional gas condensation method for synthesizing nanoparticles, however, requires excessive energy for operating the nanoparticle generator. Further, the generator is very large in size, and takes a lot of time to change its operation conditions.

The nanoparticle generator operating in this manner has difficulty in uniformly generating nanoparticles for a long period of time. Moreover, because the generator is designed to dilute the synthesized nanoparticles when they escape from the tube path after a determined period of time, the acquisition of a high concentration of nanoparticles may be accompanied with the generation of a high proportion of aggregated nanoparticles.

A simpler method for generating nanoparticles was recently suggested in Korean Patent No. 10-0857596. In the KR 10-0857596 method, while air is made to flow under the condition that a bulk material is heated on a plate heater, the nascent nanoparticles are immediately diluted with air.

Since the high-temperature heating unit is open to air, the generator is, however, difficult not only to control but also to fabricate on a small-size scale.

Particularly, the flow pattern becomes complex during dilution with surrounding air, so that a large amount of nanoparticles adhere to the inner wall of the generator and are thus lost.

Further, when the flow rate of inflow air is changed, the flow pattern and the retention time of particles change, exerting an influence on the concentration of dilution air. In addition, the loss of nanoparticles adhering to the inner wall is a factor that influences the concentration of dilution air. Accordingly, the method suffers from the disadvantage of being unable to maintain a uniform size distribution of the generated nanoparticles.

The generator according to the technique of KR10-0857596, although smaller in size than the electric furnace technique, is difficult to fabricate into a subminiature structure composed of multiple parts, and has difficulty in stably controlling the generation of nanoparticles.

Documents of Related Art (Patent document 1) Korean Patent No. 10-0857596 (Sep. 2, 2008)

BRIEF SUMMARY OF THE INVENTION

Accordingly, the present invention has been made keeping in mind the above problems occurring in the related art, and an object of the present disclosure is to provide a nanoparticle generator that is miniaturized and structured to include an internal heat-insulating tube that absorbs radiant heat at a high temperature and to quantitatively control the flow of air inside and outside the heat-insulating tube, thereby stably producing a large quantity of uniform, non-aggregated single nanoparticles.

In order to accomplish the above object, the present disclosure provides a nanoparticle generator, comprising: a body defining an internal space, with an electric insulator inserted into the internal space from a side of the body; a heat-insulating tube, internally inserted into the body, wherein the electric insulator and a local heating unit which is mounted on the electric insulator are internally inserted into the heat-insulating tube along a central axis thereof; a first inlet, provided at a side of the body, for introducing external air into the heat-insulating tube; a second inlet, provided at a side of the body, for introducing external air between the heat-insulating tube and the body; and an outlet, provided at a side of the body, for evacuating the air introduced through the heat-insulating tube into the body.

In accordance with an aspect of the present disclosure, the heat-insulating tube may be provided with a mixed gas equidistributor for inducing the uniform passage of the external air introduced through the first inlet into the body; the mixed gas equidistributor may be provided with an upper hole and a lower hole for guiding external air up and down the local heating unit, respectively; a ring-shaped, dilute air equidistributor may be provided between the heat-insulating tube and the body so as to uniformly guide the external air introduced through the second inlet into the body to an end of the heat-insulating tube; and the dilute air equidistributor may be perforated at regular intervals so that all of the perforations form a circle.

In accordance with another aspect of the present disclosure, the length of the local heating unit may be equal to or shorter than that of the heat-insulating tube; the body may be provided with a heat-sink window formed in a cylindrical form along the body; the heat-sink window may be positioned such that respective ends of both the heat-insulating tube and the local heating unit are positioned within the range of the heat-sink window; the heat-sink window may be made of a transparent material selected from among quartz and reinforced glass; and the local heating unit may have a cylindrical form.

In accordance with another aspect of the present disclosure, the local heating unit may be provided with an ion generator; the ion generator may be mounted on the local heating unit and positioned nearer to the first inlet than the material that is applied to the local heating unit such that gasification is conducted by the local heating unit; the heat-insulating tube may be provided with a differential mobility analyzer (DMA) capable of isolating nanoparticles of predetermined nanoscale sizes; and the DMA may be positioned nearer to the first inlet than a location where the material is applied to the local heating unit.

In accordance with another aspect of the present disclosure, the heat-insulating tube may be provided with a differential mobility analyzer (DMA) capable of isolating nanoparticles of predetermined nanoscale sizes; and the DMA may be positioned at an end of the heat-insulating tube.

In accordance with another aspect of the present disclosure, the nanoparticle generator may further comprise a device for quantitatively controlling the introduction of external air into the first inlet or the second inlet; and the outlet may be formed to face in a direction opposite to gravity.

The nanoparticle generator according to the present disclosure can be fabricated into a miniature form. Further, it can synthesize a great quantity of nanoparticles at medium to high concentration in a controllable manner and enrich non-aggregated, single nanoparticles.

DETAILED DESCRIPTION OF THE INVENTION

Figure 1:
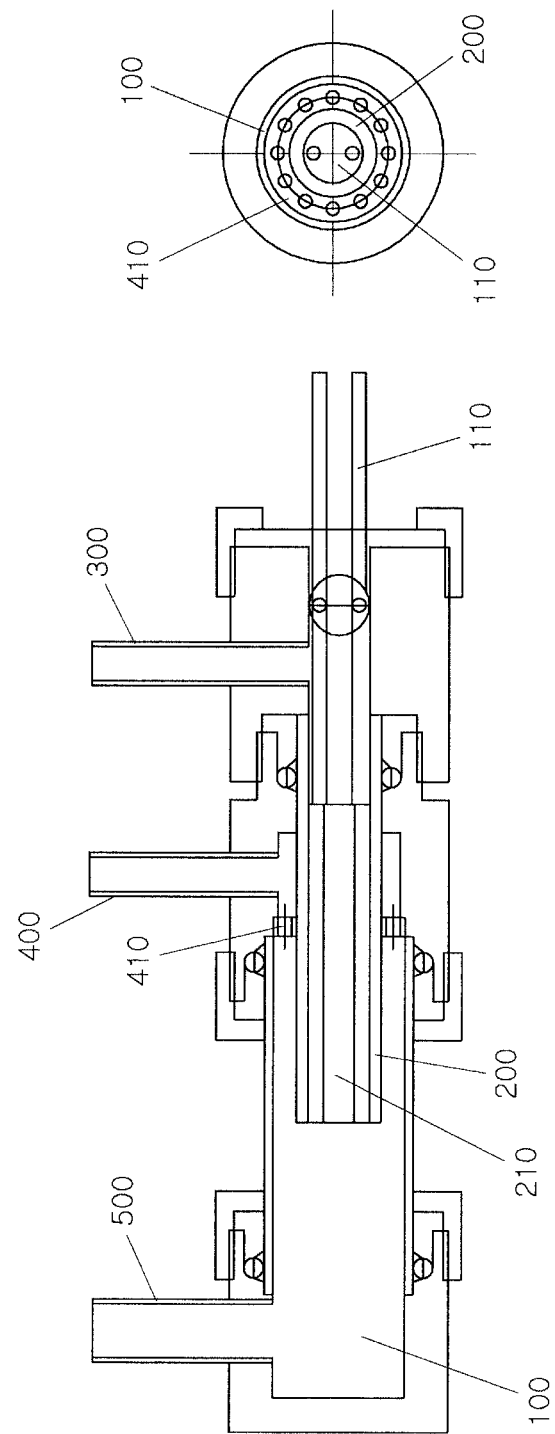
FIG. 1 is a cross-sectional view of a nanoparticle generator according to an embodiment of the present disclosure.

Embodiments of the present invention are described with reference to the accompanying drawings in order to describe the present invention in detail so that those having ordinary knowledge in the technical field to which the present invention pertains can easily practice the present invention. Meanwhile, the embodiments described in the specification and the configurations illustrated in the drawings are merely examples and do not exhaustively present the technical spirit of the present invention. Accordingly, it should be appreciated that there may be various equivalents and modifications that can replace the embodiments and the configurations at the time at which the present application is filed.

Figure 2:
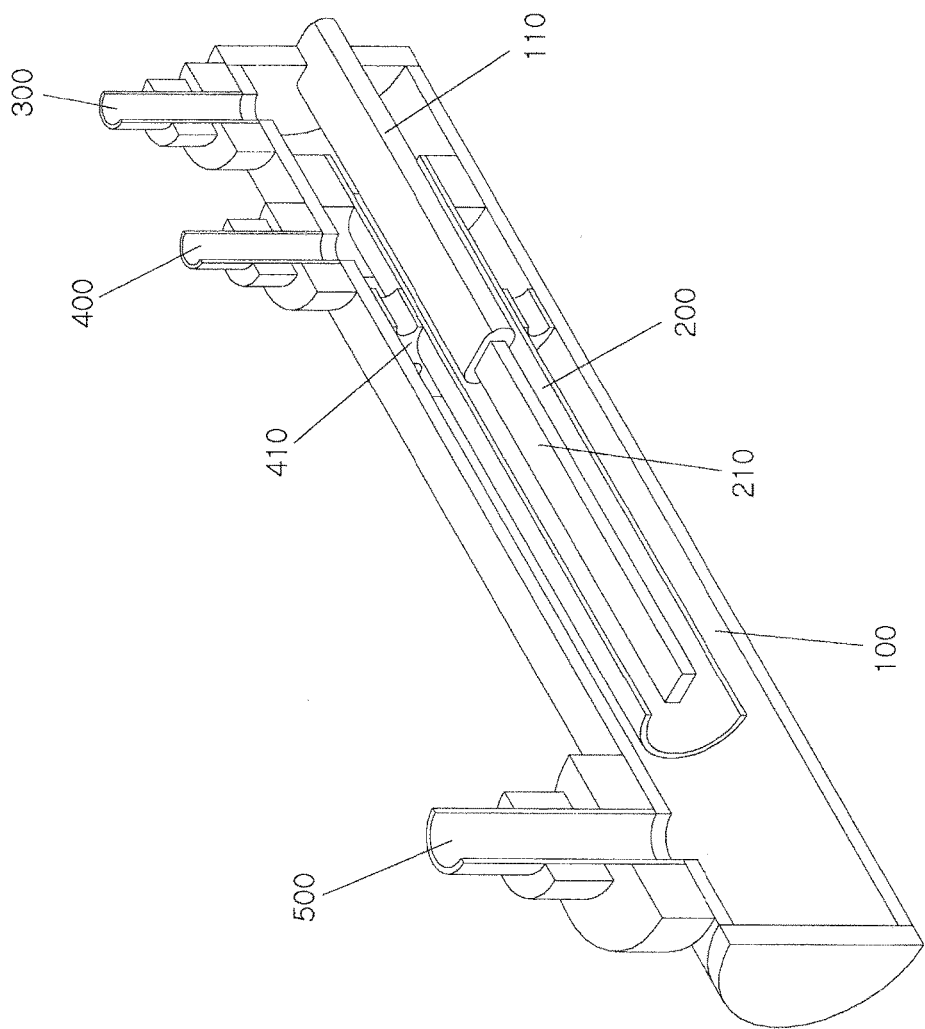
FIG. 2 is a perspective cross-sectional view of the nanoparticle generator of FIG. 1.
Figure 3:
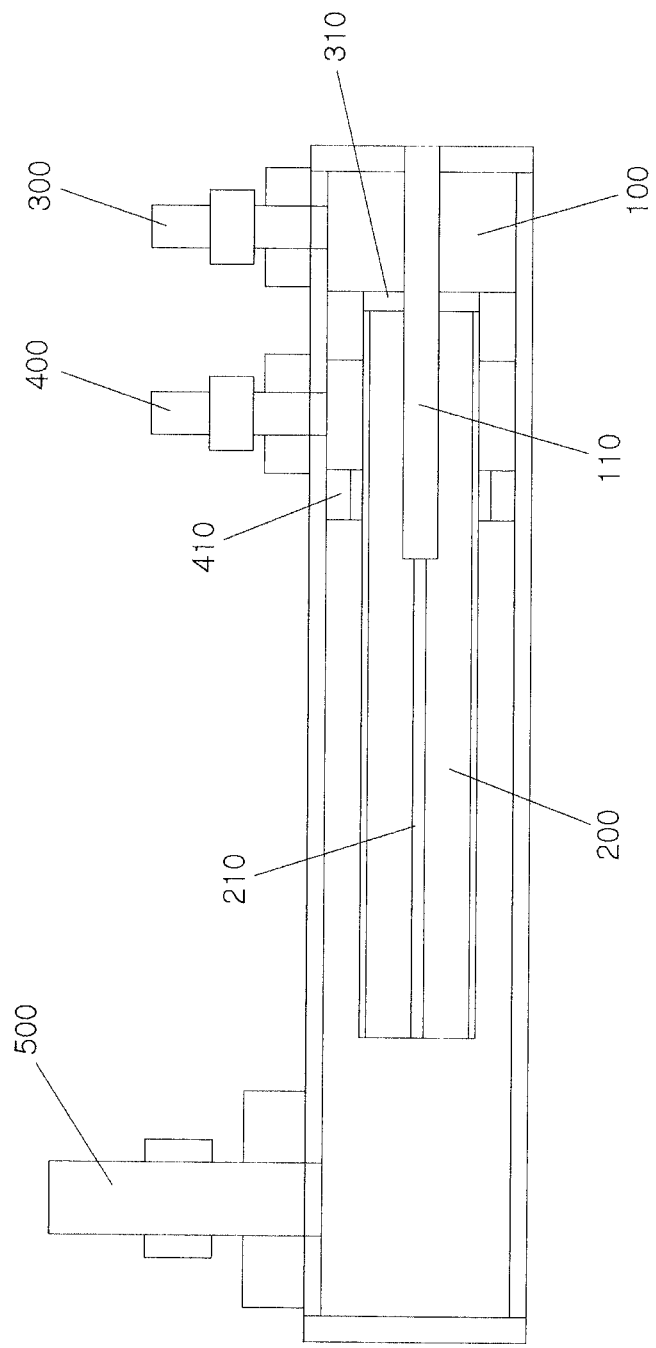
FIG. 3 is another cross-sectional view of the nanoparticle generator of FIG. 1.

FIG. 1 is a cross-sectional view of a nanoparticle generator according to an embodiment of the present disclosure, FIG. 2 is a perspective cross-sectional view of the nanoparticle generator of FIG. 1, and FIG. 3 is another cross-sectional view of the nanoparticle generator of FIG. 1.

As shown in FIGS. 1 to 3, the nanoparticle generator of the present disclosure comprises a body 100 defining an internal space, with an electric insulator 110 inserted into the internal space from a side of the body 100, a heat-insulating tube 200, internally inserted into the body 100, including a local heating unit 210 that is mounted on the electric insulator 110 and positioned along the central axis, a first inlet 300, provided at a side of the body 100, for introducing external air into the heat-insulating tube 200, a second inlet 400, provided at a side of the body 100, for introducing external air between the heat-insulating tube 200 and the body 100, and an outlet 500, provided at a side of the body 100, for evacuating the air introduced through the heat-insulating tube 200 into the body 100.

The heat-insulating tube 200 is provided at a side thereof with a mixed gas equidistributor 310 for inducing the uniform passage of the external air, introduced through the first inlet 300, into the body 100. In the mixed gas equidistributor 310, an upper hole and a lower hole are formed for guiding external air up and down the local heating unit 210, respectively.

In order to uniformly guide the external air introduced through the second inlet 400 into the body 100 to an end of the heat-insulating tube 200, a ring-shaped, dilute air equidistributor 410 is provided between the heat-insulating tube 200 and the body 100. The dilute air equidistributor 410 is perforated at regular intervals so that the perforations collectively form a circle.

Figure 4:
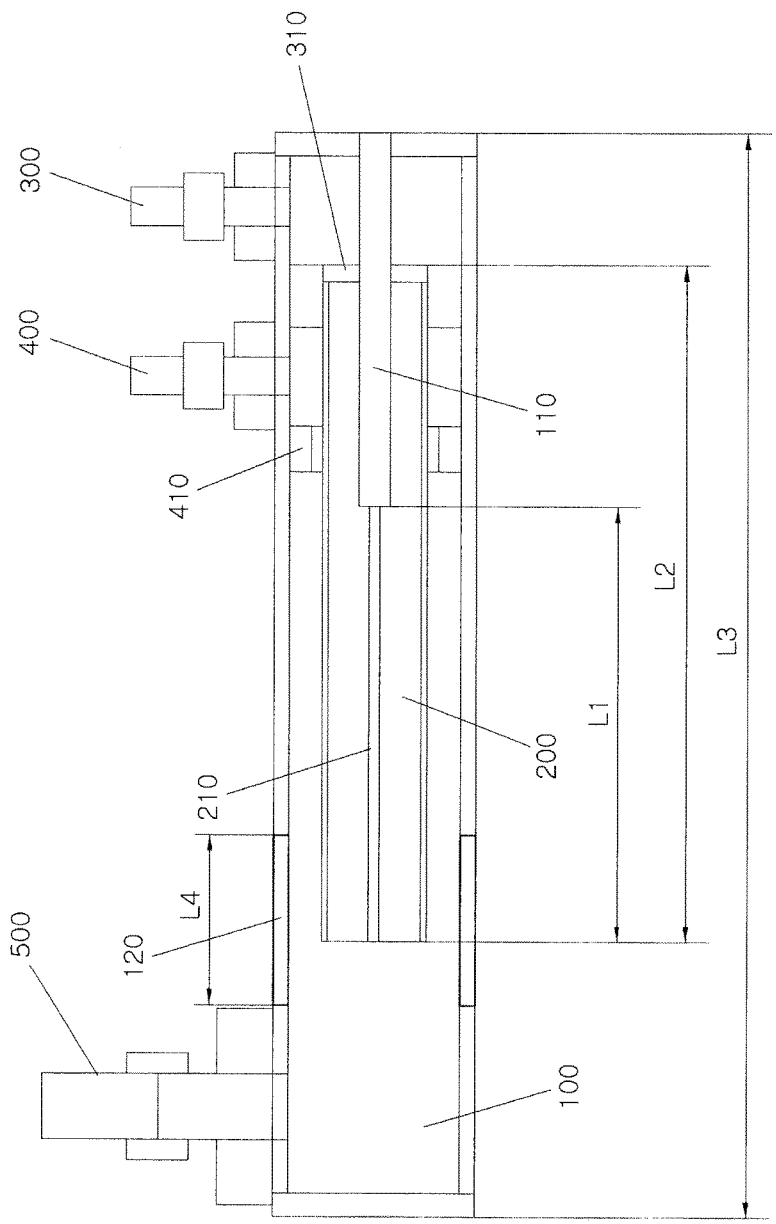
FIG. 4 is a cross-sectional view of a nanoparticle generator according to a second embodiment of the present disclosure.

The length (L1) of the local heating unit 210 is equal to or shorter than that (L2) of the heat-insulating tube 200 (FIG. 4).

Functioning to effectively shield the radiant heat generated from the surface of the local heating unit 210, the heat-insulating tube 200 is structured to cover all or part of both an upper and a lower part of the local heating unit 210.

Further, the local heating unit 210 may take a cylindrical form.

The nanoparticle generator according to a first embodiment of the present disclosure may further comprise a gas source communicating with the first inlet 300 and the second inlet 400. The gas source may be provided with a device for controlling the amount of external air influent to the first inlet 300 and the second inlet 400, and the outlet 500 of the nanoparticle generator is formed to face in a direction opposite to gravity.

The inlets through which external air is introduced into the body 100 are divided into the first inlet 300, which is connected to the heat-insulating tube 200 through which the local heating unit 210 for heating a sample to be turned into nanoparticles passes, and the second inlet 400, which is connected to a fluid path of dilute gas flowing between the heat-insulating tube and the body 100.

At an end of the heat-insulating tube, the generated nanoparticles and the dilute gas flow into each other and are mixed together. Then, the gas carries the nanoparticles to a target through the outlet 500 of the nanoparticle generator.

A common air supplier may be used to supply external air to the first inlet 300 and the second inlet 400. In this regard, the difference in pressure between the external air supplied to the two paths may cause a difference in the flow rate between the external air influent into the first inlet 300 and the second inlet 400.

Capable of absorbing radiant energy generated from the surface of the heating unit of 1,500° C. or higher, the heat-insulating tube 200 blocks the transmission of heat to the body 100 and thus prevents the temperature of the body 100 from being elevated excessively. Therefore, the body 100 can be miniaturized.

In addition, the nanoparticle generator can establish a condition under which a uniform gas flow pattern is maintained in the inside of the heat-insulating tube 200 where nanoparticles are synthesized, that is, around the local heating unit 210. Further, the flow rate of the dilute gas introduced between the heat-insulating tube 200 and the body 100 through the second inlet 400 can be changed. Thus, the concentration of the generated nanoparticles can be controlled.

The length of the heat-insulating tube 200 is controllable. To increase the concentration time of the gasified sample, the heat-insulating tube may be lengthened. On the other hand, the generation of nanoparticles of smaller sizes by decreasing the concentration time of the gasified sample can be achieved with a heat-insulating tube 200 that is shorter in length.

FIG. 4 is a cross-sectional view of a nanoparticle generator according to a second embodiment of the present disclosure. In FIG. 4, a local heating unit 210, a heat-insulating tube 200, and a heat-sink window 120 have their respective lengths (L1, L2, and L3) in the axial direction.

As shown in FIG. 4, the nanoparticle generator according to the second embodiment of the present disclosure is characterized in that the body 100 is provided with the heat-sink window 120.

The heat-sink window 120 is positioned near the end of the heat-insulating tube 200, and is formed in a cylindrical form along the body. More particularly, the heat-sink window 120 is positioned such that the ends of both the heat-insulating tube 200 and the local heating unit 210 are positioned within the axial-wise length (LA) of the heat-sink window 120.

In addition, the heat-sink window 120 may be made of a transparent material such as quartz or reinforced glass.

As stated above, the nanoparticle generator according to the second embodiment of the present disclosure is characterized in that part of the body 100 is made of a transparent material such as quartz or reinforced glass.

The heat-sink window has the effect of decreasing the temperature of the gas containing the nanoparticles because even when the heat-insulating tube 200 is too short to prevent the transmission of all of the radiant energy to the body 100, at least some of the radiant energy can be dissipated through the transparent window.

Moreover, the heat-sink window allows the user to observe with the naked eye whether the reaction is proceeding normally in the generator, and to rapidly take measures to respond to a problem if needed.

In the nanoparticle generator, the concentrated nanoparticles that are simultaneously synthesized are mixed with dilute air in a short time and are thus instantly diluted, which minimizes the aggregation of the nanoparticles.

A nanoparticle generator according to a third embodiment of the present disclosure is characterized in that the heat-insulating tube 200 is longer than the local heating unit 210.

In the nanoparticle generator according to the third embodiment of the present disclosure, the heat-insulating tube 200 is formed to be longer than the local heating unit 210. Under this condition, the ceramic tube absorbs the radiant energy, minimizing the amount of energy to be transmitted to the body 100.

When the dilute air passing outside the heat-insulating tube 200 is mixed with the nanoparticle-containing air traveling inside the heating-insulating tube 210, heat transmission through contact with the surface of the local heating unit 210 or through radiation is minimized. For this, a predetermined amount of aerosol particles can be uniformly provided, and it is possible to readily control a concentration change with dilution rate.

The length to which the heat-insulating tube 200 is inserted into the body 100 may be adjusted so as to control the retention time of the concentrated nanoparticles before dilution with air. Hence, the condensation properties can be controlled to provide the nanoparticles with a desired configuration according to the material.

A nanoparticle generator according to a fourth embodiment of the present disclosure is characterized in that the local heating unit 210 is provided with an ion generator.

The ion generator mounted on the local heating unit 210 is positioned nearer to the first inlet 300 than a location where the material is applied to the local heating unit 210 such that gasification is conducted by the local heating unit 210.

Structured to generate a multitude of ions ahead of the synthesis of nanoparticles, the nanoparticle generator according to the fourth embodiment of the present disclosure allows the nanoparticles to be highly charged with single polarity during the synthesis of nanoparticles.

Since they exist in an electrically neutral state, most nanoparticles smaller than 10 nanometers are not easy to isolate in flowing gas.

If charged, particles can be easily isolated with an electric field even in flowing gas. Thus, the electrical isolation of charged particles finds applications in various fields.

A nanoparticle generator according to a fifth embodiment of the present disclosure further comprises a differential mobility analyzer (DMA) capable of isolating nanoparticles of predetermined nanoscale sizes, which may be provided at the outlet of the heat-insulating tube 200 or the outlet 500 of the nanoparticle generator.

The nanoparticle generator according to the fifth embodiment of the present disclosure is structured such that a simple DMA is provided at the rear end of the generator to isolate nanoparticles of desired sizes.

Most nanoparticles with a size of about 10 nm or less exist in an electrically neutral state or take a charge of +1 or −1.

Particularly, since a high proportion of nanoparticles generated at high temperatures are positively or negatively charged, the particles can advantageously be enriched when they pass through a differential mobility analyzer (DMA).

A system in which particles can be separated at a distance under an electric field allows for the isolation of particles of equal sizes.

Equipped with a DMA, therefore, the nanoparticle generator according to the fifth embodiment of the present disclosure can isolate enriched nanoparticles of predetermined sizes.

What is claimed is:

1. A nanoparticle generator, comprising:
   a body defining an internal space, with an electric insulator inserted into the internal space along a central axis of the body;
   a heat-insulating tube, internally inserted into the body, wherein the electric insulator and a local heating unit which is mounted on the electric insulator are internally inserted into the heat-insulating tube along a central axis thereof;
   a first inlet, provided at a side of the body, for introducing first external air into a first portion of the internal space defined by the body, wherein the first external air, introduced through the first inlet into said first portion of the internal space, is introduced into the heat-insulating tube, and the first portion is separate from another portion of the internal space defined by the body;
   a second inlet, provided at said side of the body, for introducing second external air between the heat-insulating tube and the body; and
   an outlet, provided at said side of the body, for evacuating, via said another portion of the internal space, the first external air which is introduced through the heat-insulating tube into said another portion of the internal space.

2. The nanoparticle generator of claim 1, wherein the heat-insulating tube is provided with a mixed gas equidistributor for inducing uniform passage inside the heat-insulating tube of the first external air.

3. The nanoparticle generator of claim 2, wherein the mixed gas equidistributor is provided with an upper hole and a lower hole for guiding the first external air up and down the local heating unit, respectively.

4. The nanoparticle generator of claim 1, wherein a ring-shaped, dilute air equidistributor is provided between the heat-insulating tube and the body to uniformly guide the second external air, introduced through the second inlet, into the body to an end of the heat-insulating tube.

5. The nanoparticle generator of claim 4, wherein the dilute air equidistributor is perforated at regular intervals such that the perforations collectively form a circle.

6. The nanoparticle generator of claim 1, wherein the local heating unit is not greater in length than the heat-insulating tube.

7. The nanoparticle generator of claim 1, wherein the body is provided with a heat-sink window formed in a cylindrical form along the body.

8. The nanoparticle generator of claim 7, wherein the heat-sink window is positioned such that respective ends of both the heat-insulating tube and the local heating unit are positioned within an axial-wise length of the heat-sink window.

9. The nanoparticle generator of claim 7, wherein the heat-sink window is made of a transparent material selected from among quartz and reinforced glass.

10. The nanoparticle generator of claim 1, wherein the local heating unit has a cylindrical form.

11. The nanoparticle generator of claim 1, wherein the local heating unit is provided with an ion generator.

12. The nanoparticle generator of claim 11, wherein the ion generator is mounted on the local heating unit and is positioned nearer to the first inlet than a location where a material is applied to the local heating unit such that gasification is conducted by the local heating unit.

13. The nanoparticle generator of claim 12, wherein the heat-insulating tube is provided with a differential mobility analyzer (DMA) capable of isolating nanoparticles of predetermined nanoscale sizes.

14. The nanoparticle generator of claim 13, wherein the DMA is positioned nearer to the first inlet than a location where the material is applied to the local heating unit.

15. The nanoparticle generator of claim 1, wherein the heat-insulating tube is provided with a differential mobility analyzer (DMA) that is capable of isolating nanoparticles of predetermined nanoscale sizes.

16. The nanoparticle generator of claim 15, wherein the DMA is positioned at an end of the heat-insulating tube.

17. The nanoparticle generator of claim 1, further comprising a device for quantitatively controlling introduction of the first external air or the second external air into the first inlet or the second inlet, respectively.

18. The nanoparticle generator of claim 1, wherein the outlet is formed to face in a direction opposite to gravity.

* * * * *